United States Patent [19]
Coggins

[11] Patent Number: 5,792,047
[45] Date of Patent: Aug. 11, 1998

[54] PHYSIOLOGICAL PARAMETER MONITORING AND BIO-FEEDBACK APPARATUS

[76] Inventor: George Coggins, 319 Spruce St., Redwood City, Calif. 94063

[21] Appl. No.: 784,125

[22] Filed: Jan. 15, 1997

[51] Int. Cl.⁶ ..................................................... A61B 5/02
[52] U.S. Cl. .......................... 600/300; 600/545; 128/905
[58] Field of Search ...................................... 600/545, 544, 600/546, 483, 300, 324, 450, 485, 508, 524; 128/905; 434/236, 238, 262

[56] References Cited

U.S. PATENT DOCUMENTS

| | | | |
|---|---|---|---|
| 4,140,997 | 2/1979 | Brady | 600/545 |
| 4,170,225 | 10/1979 | Crigler et al. | 600/545 |
| 4,800,893 | 1/1989 | Ross et al. | 600/545 |
| 5,101,809 | 4/1992 | Daffer et al. | 607/104 |
| 5,319,250 | 6/1994 | Windsor | 307/139 |
| 5,343,871 | 9/1994 | Bittman et al. | 600/545 |
| 5,415,167 | 5/1995 | Wilk | 600/427 |
| 5,437,278 | 8/1995 | Wilk | 600/425 |
| 5,544,651 | 8/1996 | Wilk | 600/515 |
| 5,553,609 | 9/1996 | Chen et al. | 600/483 |
| 5,596,994 | 1/1997 | Bro | 600/545 |

*Primary Examiner*—Jennifer Bahr
*Assistant Examiner*—Stephen Huang
*Attorney, Agent, or Firm*—Goldstein & Associates

[57] ABSTRACT

A bio-feedback system to support the collection of a plurality of physiological parameter values of a subject being monitored. The physiological parameter values collected are processed to determine and present to the subject a continuously updated succession of presentation states, possibly multimedia in nature, in order to attempt to enhance the bio-feedback capability of the system. The system includes a digitizing camera arranged to continually capture an image of the subject. The presentation states, which include the captured image of the subject, are accented by color accents including curved bands of color coextensive with and juxtaposed to the outline of the image of the subject. The color of the bands may be appropriately altered in a predefined manner as determined by changes in the physiological parameter values collected and processed.

13 Claims, 6 Drawing Sheets

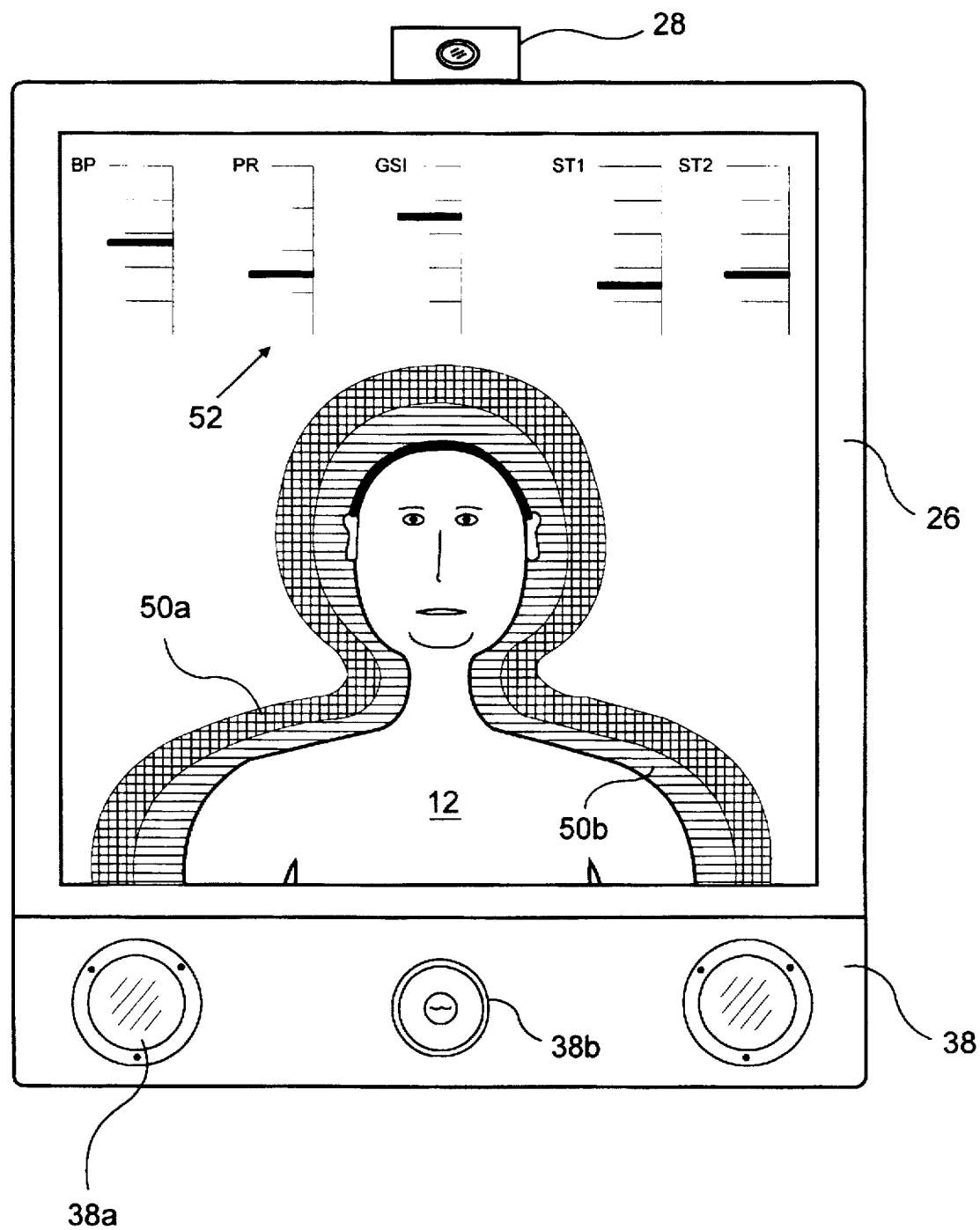

PHYSIOLOGICAL PARAMETER MONITORING AND BIO-FEEDBACK APPARATUS

BACKGROUND OF THE INVENTION

1. Field Of The Invention

The invention relates to systems that monitor physiological parameters, and more particularly, to a complex and modular system to collect and store physiological parameter values as information, and subsequently (generally in real-time) produce and present related and representative information to a subject that is generated or selected based on the collected and processed parameter values.

2. Background and Objects of the Invention

The study of biofeedback, which has been known for many years, involves the use of sensing elements to monitor one or more physiological parameters of a subject, such as temperature, heart rate, blood pressure, and the like, and using the monitored (and collected) physiological parameter information to provide a means of feedback. The information that establishes the feedback is typically observed by the subject whose physiological parameters are being collected, and to a lesser extent, an individual supervising the session/experiment. An important characteristic of bio-feedback type systems is the manner and composition of the presented information. The composition usually includes scenes of nature, animals, still portraits, and the like. The use of colors may include providing monotone regions, color patterns, or color accents. Regardless of the manner of displaying the presented information, the goal is typically to allow the individual to be cognizant his current bio-physical state, and support the possible altering and self-regulating of said state by the subject.

There are many examples of prior art biofeedback systems that may be cited herein. One such system is described in U.S. Pat. No. 5,343,871 to Bittman et al, which also provides a very detailed summary of many representative prior art systems. The Bittman system, as well as others known in the art, include a variety of sensors to sense a plurality of physiological parameters. These "input devices" may be termed transducers. The collected physiological parameter data, usually stored in digital form, is then used to produce and present to the subject under observation a predetermined and/or representative response. The presentation of the response may be via one or more of analog and digital meters, video displays, projection units, audio speakers, strobed or flashing lights, and the like. The characteristics, features, and goals provided by each of the systems varies over a significant breadth. Some simply provide simple meter-observed indications (and biofeedback), without the use of other more sophisticated audio and/or video forms of feedback. Some do not record any of the collected physiological parameter data, while others record the data in complex data sets in massive databases, and may at the same time determine and present related goals (say for relaxation training) or statistically reduced results (say by way of single and multi-dimensional charts, tables, histograms, etc).

However, there is a need for systems which will monitor traditional physiological parameters, as well as electromagnetic and infrared fields/waves which are emitted either directly or by reflection from the subject being monitored. Further needed is a complex multimedia presentation based on sensed physiological parameters and reduced results, which may be presented to the subject via one or more output devices providing audio, visual, and other forms of presentation. Their is a also need for a system which will monitor and record may aspects of the session including video records, audio records, and full or partial physiological parameters profiles. When considering the problems and drawbacks of known systems to provide this level of biofeedback monitoring, presentation, and storage, there is a need for improved and advanced arrangements that will enable sophisticated biofeedback therapy and research.

Objects of the present invention are, therefore, to provide new and improved biofeedback means with associated methods of use and operation having one or more of the following capabilities, features, and/or characteristics:

- full spectrum physiological parameter sensors, including contact and non-contact multi-element array sensors;
- monitoring a detailed physiological state of one or more subjects in real-time;
- recording the detailed physiological state for later playback and/or analysis;
- sensing electromagnetic and IR waves emitted by the subject being monitored;
- provide continuous real-time cause and effect monitoring of many physiological parameters including body temperature, heart/pulse rate, blood pressure, pH level of perspiration, skin conductivity or resistance, skin shade (blush) changes, and the like; and
- provide to the subject visually displayed information, including the image of the subject, to attempt to enhance the ability of the subject to observe and be cognizant of the parameter values collected and determined, and more generally the physiological state (of the subject);
- graphically present displays of data collected including parameter values, averages, moving averages, trends and slopes, pie and bar charts, and other known presentations of all parameters monitored and determined via the sensors.
- enhance the "feedback" provided to the subject to attempt to enable the subject to alter and possibly self-regulate his or her physiological state.

The above listed objects, advantages, and associated novel features of the present invention, as well as others, will become more clear from the description and figures provided herein. Attention is called to the fact, however, that the drawings are illustrative only. Variations are contemplated as being part of the invention, limited only by the scope of the appended claims.

SUMMARY OF THE INVENTION

In accordance with the invention, a bio-feedback system is provided to enable the determination and collection of a plurality of physiological parameter values of a subject being monitored. The physiological parameter values collected, stored, and processed are employed to present to the subject continuously updated presentation states to enable the subject to attempt to determine and possibly self alter the possibly subject's present physiological state. The system is comprised of a digitizing camera arranged to continually capture the image of the subject, a plurality of physiological parameter sensors with each sensor arranged to sense at least one physiological parameter value of the subject, a computing means, and a presentation means. The computing means is operatively coupled to the digitizing camera to receive therefrom the image information of the subject. The computing means further is operatively coupled to the sensors to enable the collection of physiological parameter value information sensed thereby. The presentation means enables the presentation to the subject of the presentation states, including the image of the subject, as generated by the computing means. The presentation states including and indicating at least one of the current physiological parameter values, the current physiological state of the subject, and trends in the changes of the physiological state and parameter values being sensed (which are displayed along with the image of the subject).

The information is sensed by the sensors and presented to the subject via the presentation states to attempt to enhance the ability of the subject to self regulate his/her current physiological state. The computing means, possibly including an external mass storage unit, may be capable of storing image and physiological parameter information for each subject monitored which may at a subsequent time be accessed to compare at least one stored physiological state to at least one other known physiological state.

BRIEF DESCRIPTION OF THE DRAWINGS

In the drawings, like elements are depicted by like reference numerals. The drawings are briefly described as follows.

FIG. 4 depicts an embodiment of a presentation state illustrating a plurality of the key features thereof.

LIST OF REFERENCE NUMERALS USED IN THE DRAWINGS

10—physiological parameter monitoring system
12—subject (individual being monitored, ...)
16—contact sensors (including 16a to 16e)
18—non-contact sensors (including 18a to 18c)
18d—interface circuitry
22—computing means
22a—multiplexer
26—display unit
28—video camera
30—storage unit
34—printer
36—operator and/or observer station (desk/chair)
36a—subject chair
38—sound output unit
38a—sound output device
38b—light producing device
40a—coupling (contact sensors)
40b—coupling (non-contact sensors)
40c—coupling (display unit and video camera)
40d—coupling (multiplexer to computer)
42—vibration producing means
50a, 50b—color accents
52—parameter readout displays
60 to 100—flowchart blocks

DETAILED DESCRIPTION OF THE PREFERRED EMBODIMENTS

It is important to establish the definition of several important terms that will be used throughout this disclosure. The terms "physiological parameter" and "parameter" will be applied to indicate any physiology related quantity, that may be monitored to determine one or more quantitative physiological levels and/or activities associated with an individual (the subject). Collectively, a plurality of physiological parameter values may be referred to as "physiological parameter information", as can a data base of parameter values collected and stored over a known time interval. A stored or measured collection of parameter values may be said to define a (stored or current) physiological state of a subject. Thus, a physiological state of a given subject may be defined by considering, and possibly combining, a plurality of parameter values. Another important term to be defined is that of a "presentation state". A presentation state is generated for presenting information to the subject. The information may be comprised of parameter values measured and other determined items (possibly statistical in nature), in combination with the image of the subject and associated color (and possibly texture-like accents). Color accents will be defined as including (colorful) additions accentuating a displayed image of the subject. As such, they (the accents) will include at least one curved band of color coextensive with and juxtaposed to the outline of the image of the subject, thereby presenting an aura associated with and representative of the physiological state of the subject. Finally, the terms "interactive feedback" and "interactive bio-feedback", as applied to a system or apparatus, will be defined as a device, system, etc., which permits the subject to observe, via presented information, his or her physiological state. Thereby possibly enabling and enhancing the ability of the subject to affect, alter, and self-regulate the observed physiological state (as well as changes and trends occurring therein).

Figure 1:
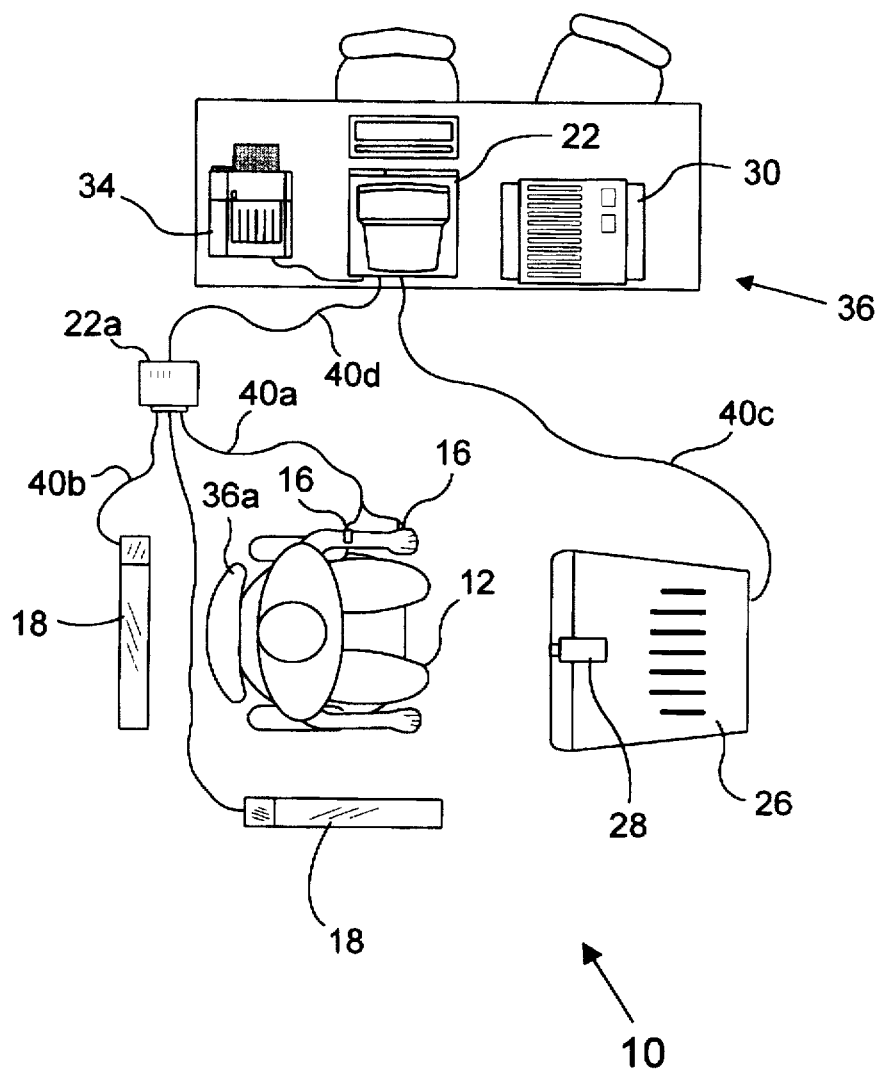
FIG. 1 provides a plan view of an embodiment of a system in accordance with the present invention.

Referring now to FIG. 1, there is depicted an arrangement in accordance with the present invention. Shown is a bio-feedback system 10 configured to monitor a plurality of physiological parameters and collect the associated parameter value information. Included are a plurality of sensors comprised of contact sensors 16 and non-contact sensors 18, each of which may be arranged as an array of sensing elements. (Arrays of sensors will generally be employed to increase the sensitivity of the measurement of one or more physiological parameters to be observed and possibly displayed.) A multiplexing device, such as multiplexor 22a, may be included to support the operative couple the sensors 16/18 to a computing means 22. Computing means 22 may be provided by any suitable general purpose computer (e.g., a PC or the like), or alternately, by a special function (embedded) computer. Additional details of the operation and functions provided by the computing means 22 will be more completely addressed below. The system 10 may further include a display unit 26, a color printer 34, an external (to the computing means 22) storage unit 30, a digitizing video camera 28, and a plurality of suitable couplings including 40a, 40b, 40c, and 40d, which are utilized to operatively couple and interconnect the various components of system 10, as shown.

The arrangement of FIG. 1 enables the image of the subject, along with a variety of physiological parameter value information to be received by the computing means and stored and processed (as required). The image captured by the video camera 28 and information (from the sensors and as determined by the computing means 22) may then be displayed on the display unit 26 for the subject 12 to observe. This arrangement enhances the ability of the subject 12 to possibly self regulate his/her current physiological state by enabling the subject to observe changes and trends in the subjects physiological state in real-time, thereby providing the "feedback" mechanism required with bio-feedback devices and systems. It should be noted that although the subject 12 is shown in a seated position, it is contemplated that the subject 12 may be in a number of possible positions. For example, a possibly preferred arrangement may have the subject 12 laying down with the video camera 28 positioned overhead (of the subject).

Figure 2:
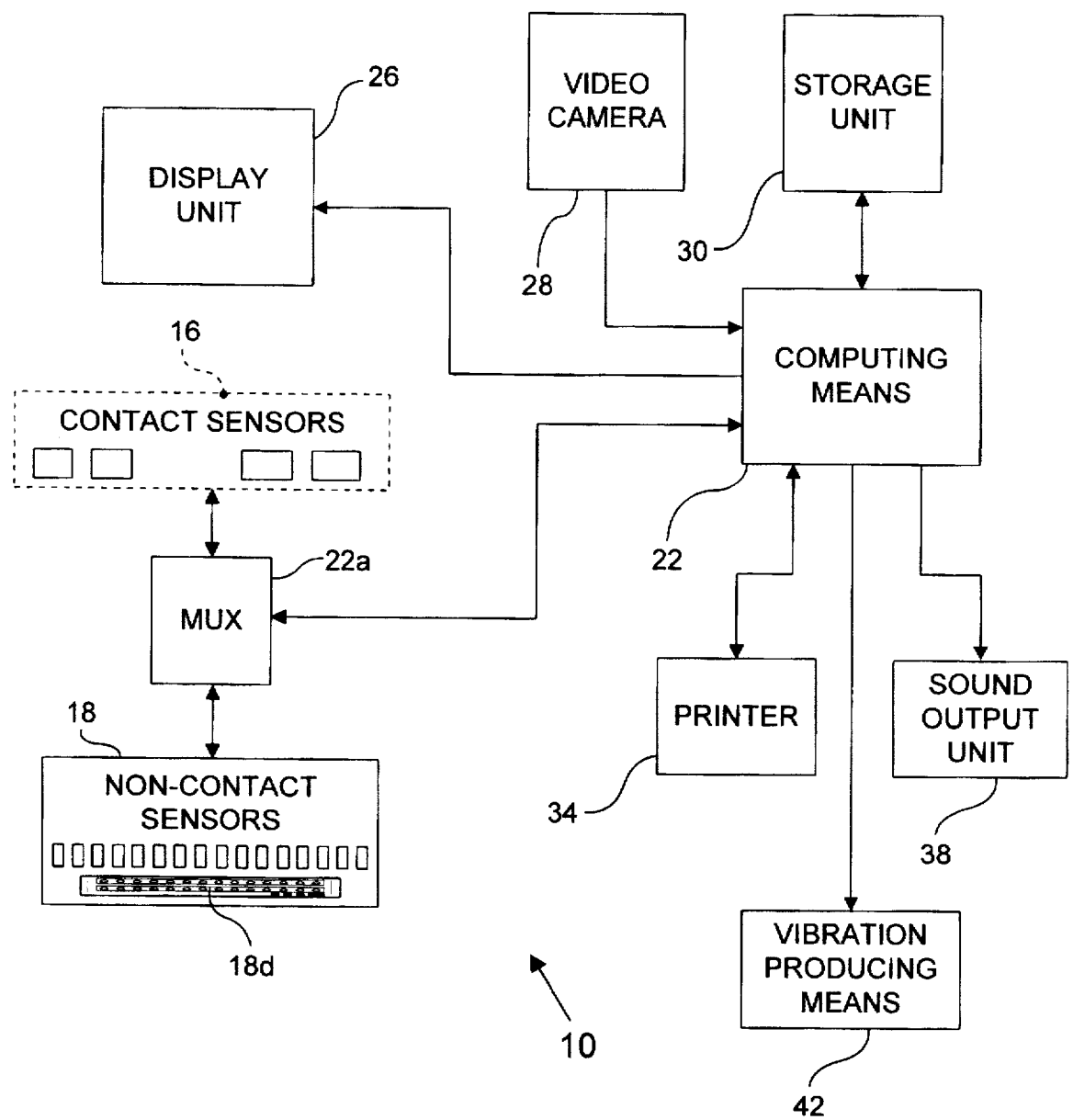
FIG. 2 is a functional high level block diagram on an embodiment of the invention.
Figure 3A:
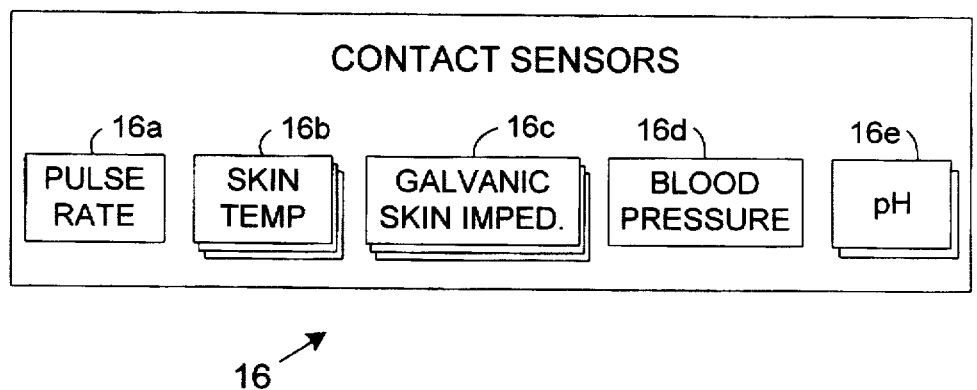
FIGS. 3A and 3B provide embodiments of the contact and non-contact sensor configurations that may be employed with the embodiment of FIG. 2.
Figure 3B:
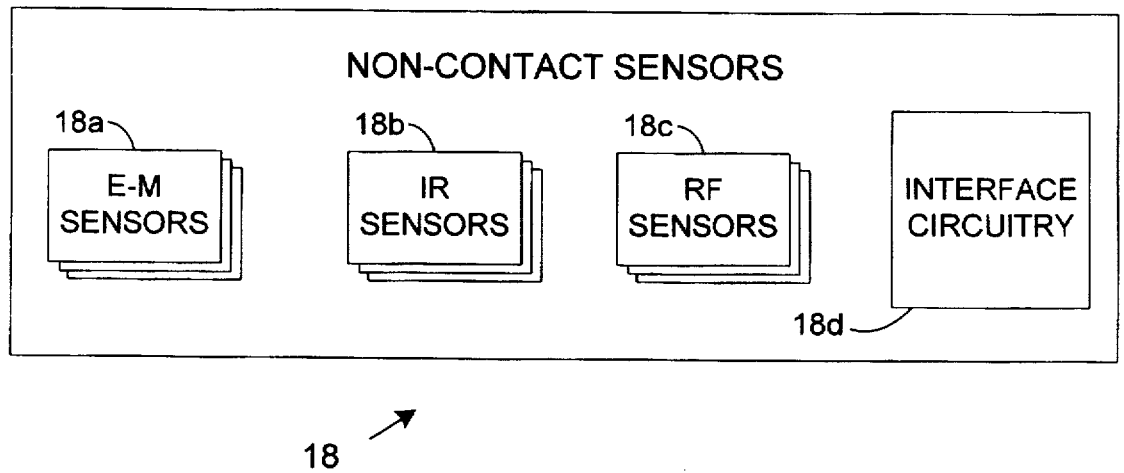

Referring now to FIG. 2, there is provided a functional high level block diagram on an embodiment of the invention. Shown are the sensors comprised of a plurality of contact (type) sensors 16 and at least one non-contact sensor arrangement 18 that may include a plurality of sensing elements and interface circuitry 18d (possibly including a multiplexer). The contact sensors 16 and the non-contact sensors 18 may be interfaced to the computing means 22 by the multiplexer 22a, as required. The multiplexer 22a may also include signal conditioning and conversion circuitry. It should be noted that, as shown in FIG. 3A, the plurality of contact sensors may include one or more sensors of each type selected from the group including pulse rate sensors 16a, skin temperature measuring sensors 16b, galvanic skin impedance sensors 16c, blood pressure sensors 16d, and pH sensors 16e. These and other sensing devices are well known in the art. The non-contact sensors 18, as depicted in FIG. 3B, may generally be arranged in arrays of such sensors to increase the sensitivity and/or directional characteristics of the "array". The non-contact sensors (and arrays) may include one or more sensors of each type available from a group including infrared (IR) emission sensors 18b, high-frequency R-F emission sensors 18c, and E-M field emission sensors 18a. Accordingly, a diverse plurality of sensors support the collection of physiological parameter information of the subject 12 (via the contact and non-contact sensor/sensing elements).

Turning again to FIG. 2, there is further shown a video camera 28 coupled to the computing means 22. The video camera 28, which in a preferred embodiment would be provided by a high speed digitizing (e.g., CCD) video camera, is suitably arranged to continually (in a periodic fashion) capture the image of the subject 12 being monitored. The display unit 26, like the video camera 28, is also coupled to the computing means 22 and will receive therefrom the images of the subject, along with other parameter information. The display unit 26, and possibly the sound output unit 38, which may be termed an embodiment of a "presentation means", may be employed by the computing means 22 to support the presentation of information to the subject. The information being provided in the form of the presentation states, and including the subject image captured by the video camera 28. The presentation states indicating at least one of current physiological parameter values being collected, and other information indicating the current physiological state of the subject (determined via collecting and processing of parameter information), and trends in the changes of the physiological state and/or parameter values being sensed. Accordingly, the information is sensed by the sensors and presented to the subject 12 via the presentation states to attempt to enhance the ability of the subject 12 to self regulate his/her current physiological state. That is, the system 10 provides an interactive bio-feedback "link", wherein the subject 12 can monitor his/her current physiological state and subsequently possibly alter or self-regulate (via the feedback) various physiological parameters being sensed and presented. The computing means 22 is contemplated to further support the storing of image and physiological parameter information for each of a plurality of subjects monitored. The stored information may at a subsequent time be accessed to compare current or other known (possibly stored) physiological states. The external storage unit 30, which may be provided in addition to other internal storage devices of the computing means 22, would be included as a high capacity storage archive. For example, the storage unit 30 may in a preferred embodiment be provided by an array of high-speed and high-capacity optical drives systems. Such a system would be able to store many many subject' physiological parameter sets. To further enhance the bio-feedback link provided to the subject 12, suitable mechanical devices, such as a vibration producing means 42, may be provided with the system 10. The mechanical devices may produce vibrations that are suitably coupled to the subject 12 to enable the system to vary the level (magnitude) of vibrations as the physiological state of the subject varies.

In order to provide for hard copy printouts of images or physiological information collected, a printer 34 is provided, as shown in FIGS. 1 and 2. The printer would in a preferred embodiment be provided by a color (capable) printer device, such as a color laser printer, or the like. The hard copy printouts may be simple records of the presentation states output to the subject, or other much more detailed records of all the information collected and determined during a bio-feedback session.

It must be noted that the embodiments provided in FIGS. 1 and 2 are illustrative only. Skilled persons may provide modifications and additions which provide the same essential functionality via alternate architectures. All such modifications are contemplated as being within the scope of the present invention, especially those systems combining "accents" and other information with the image of the subject 12 to indicate the current physiological state (condition) of the subject -to the subject.

Turning now to FIG. 4, there is illustrated an embodiment of a presentation state of the present invention. The display unit 26 is provided to enable text, graphics, color accents, and images, to be presented to the subject. As depicted, the image of the subject 12 is accented by color accents, including color accent 50a and color accent 50b. The color accents may be employed so that the color (or hue/tint) may be varied as the associated physiological parameter value sensed varies. For example, as shown the accents displayed include at least one curved band of color, that is coextensive with and juxtaposed to the outline of the image of the subject 12 thereby presenting an aura, or the like, that is associated with and representative of current physiological parameters values or a general physiological state (being sensed). Accordingly, the color (or tint/hue) of the bands may be appropriately altered in a predefined manner as determined by the parameter information received and processed by the computing means to provide the desired feedback to the subject. It is contemplated that a presentation state may include a series of parameter readout displays 52, which may be provided to indicate, for example, the actual (reading of) blood pressure, skin temperature, pulse rate, and the like, of the subject. Although not shown each "readout" may include an actual numerical value measured or figure of merit, say below the indicating graphic, and have an associated "arrow" indicating if the parameter is increasing or decreasing (also not shown). Also shown in FIG. 4 is a sound output unit 38 having at least one audio output device 38a and one light producing device 38b. The audio output device 38a may be provided by a speaker, or the like, suitably configured to supply audio information to the subject. A well known parameter generally indicated to the subject 12 via a speaker is the subject's heart beat. Other sounds may be provided wherein the level (loudness) or the frequency (pitch) of the sounds are altered as the physiological parameter values of the subject vary. As such, the display unit 26 and the sound output unit 38 support the delivery of any appropriate sound, text, or graphic, that may be included with the image of the subject 12 to further enhance the feedback provided to the subject. Similarly, the light producing device 38b may included further enable the subject to sense levels or changes in parameter values.

It must be understood that the presentation state illustrated in FIG. 4 is one of many arrangements possible. For example, simple digital "readouts" may be provided (on screen or with separate output units) to indicate the precise level of each physiological parameter sensed and/or determined. Similarly, a single band may be segmented to represent a plurality of parameters along said band, wherein the color (or pattern, texture, etc.) of each segment may be altered independently as the associated parameter value varies. In addition, the image displayed may be a bust (as shown), or for example, capture the individual from the waist up. Those skilled in the art may provide other arrangements of the presentation states of the present invention to enable and enhance the feedback indications provided to the subject. These arrangements, in combination with the image of the subject and suitable color accents, are contemplated as being within the scope of the present invention.

Figure 5A:
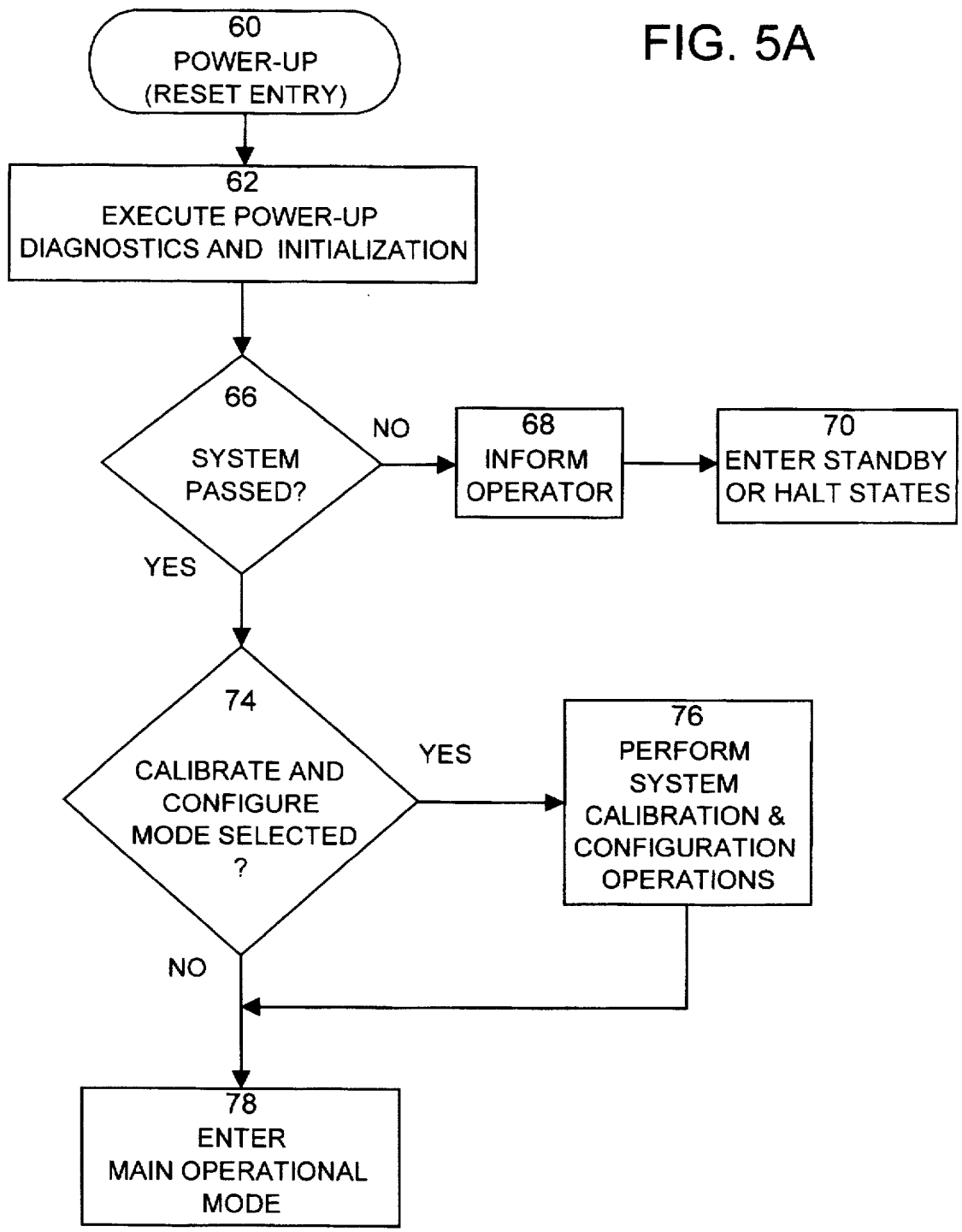
FIG. 5A and 5B are high level flowcharts of an operating process that may be employed with the embodiments of the invention shown in FIGS. 1 and 2.

Referring now to FIG. 5A, there is illustrated a high level flowchart of an operating process that may be employed with the embodiments of the invention shown in FIGS. 1 and 2 during power-up or system reset. The process begins with the system 10 being powered-up at 60. The system 10 may then execute at 62 one or more diagnostics tests to verify the operation of the hardware and/or software of the system 10, and perform any required system initialization. If at 66 the system diagnostic determines an error has occurred, the operator is informed and the system 10 may be placed in a standby or halt state. If the system passes the diagnostic checks, at 74 the system 10 may be placed into a calibration and configuration mode. The calibration may be required to adjust and set reference points for the physiological parameters to be sensed, or to configure the system 10 for the particular sensors and other devices/units included with an embodiment of the system 10. Once the calibration and configuration of the system 10 is performed at 76, the system 10 may enter a main operating mode at 78. An embodiment of the main operating mode 78 will be addressed below while making reference to FIG. 5B.

It should be noted that the calibration mode may be selected via the keyboard of the computing means 22 (as shown in FIG. 1), or by way of a "menu" selection or icon made available to the user by a display included with said computing means. Alternately, a function key may be employed and available at any point to place the unit in a cal/config mode.

Figure 5B:
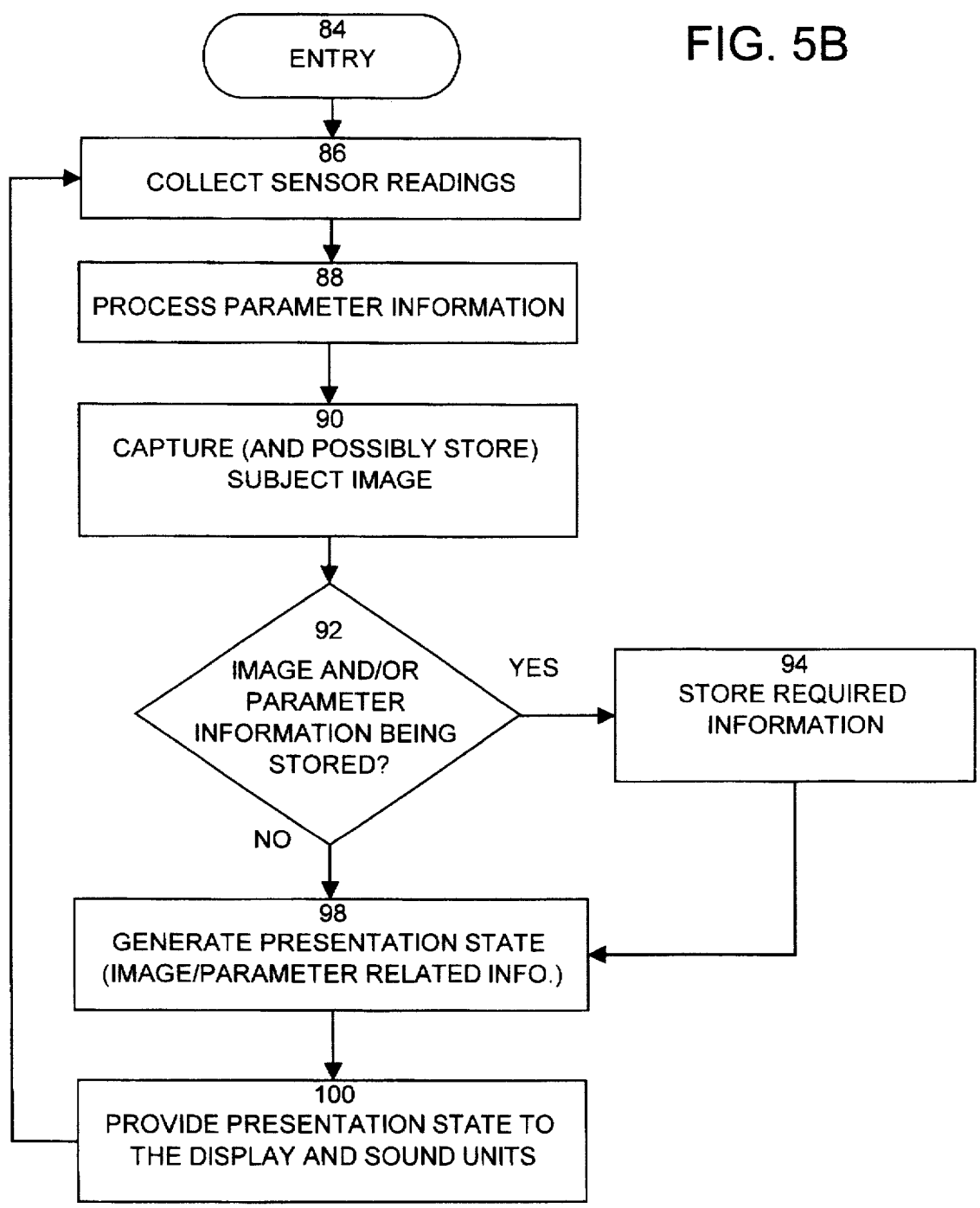

Turning now to FIG. 5B, the main operating mode is entered at 84. It is assumed that the subject 12 has been appropriately fitted with the needed contact sensors, and the system 10 is ready to commence operation. At 86, sensor readings (i.e., physiological parameter values) are collected by the computing means 22 and processed at 88. The processing may involve simple scaling or normalizing operations, or may involve complicated analysis and computations to determine other values or items. For example, a combination of parameters sensed may be utilized to determine an "overall" physiological state indicator (of the subject), which may be presented to the subject 12 via one or more determined presentation states. Next, at 90 the image of the subject 12 is captured, and possibly stored. If a "log" of the session is being made (stored), as determined at 92, the information may be stored using an internal mass storage device of the computing means 22, or using an external storage device, such as storage unit 30 (of FIGS. 1 and 2). At 98, a presentation state is generated and at 100 presented to the subject 12 being monitored.

It is important to understand the operational processes of FIGS. 5A and 5B may be altered and still provided the fundamental features of the present invention. Further, it must be understand, that the order of the steps illustrated in FIGS. 5A, and in particular in FIG. 5B, may be altered without departing from the spirit and scope of the process provided. For example, the capturing of the image at 90 may actually precede the collection of sensor readings at 86. Skilled persons may provide other yet other modifications to the processed of FIGS. 5A and 5B. Accordingly, modifications of this form, including additional steps, are contemplated as being within the scope of the invention.

The architectural and operational embodiments described herein are exemplary of a plurality possible to provide the same (or equivalent) general system operation and features. Therefore, while there have been described the currently preferred embodiments of the present invention, those skilled in the art will recognize that other and further modifications may be made without departing from the present invention, and it is intended to claim all modifications and variations as fall within the scope of the invention.

What is claimed is:

1. A bio-feedback system to enable a determination and collection of a plurality of physiological parameter values of a subject being monitored, the physiological parameter values collected, stored, and processed to enable a presentation to the subject of a continuously updated presentation state representative of a current physiological state of the subject to attempt to enhance an ability of the subject to be aware of and possibly self-alter the subject's present physiological state, the bio-feedback system comprising:

(a) a digitizing camera arranged to continually capture an image of the subject;
   (b) a plurality of physiological parameter sensors, each sensor arranged to sense at least one physiological parameter value of the subject being monitored;
   (c) computing means, having the digitizing camera operatively coupled thereto to receive from the digitizing camera each captured image of the subject, and further having operatively coupled thereto the sensors to enable collection of physiological parameter values determined by the sensors that compose the physiological state; and
   (d) presentation means to enable a presentation to the subject of presentation states including the captured image of the subject along with other information including physiological parameter values sensed, information computed from physiological parameter values sensed, and a trend in changes of at least one physiological parameter values being sensed;
   (e) the presentation states presented to the subject via the presentation means in order to attempt to enhance the ability of the subject to possibly alter and self-regulate the subject's current physiological state.

2. The bio-feedback system according to claim 1, where the presentation means presents a continuously updated presentation state that includes at least one of text, graphics, sound, and vibration, in addition to the captured image of the subject having color accents associated therewith, wherein the color accents displayed include at least one curved band of color coextensive with and juxtaposed to an outline of the image of the subject thereby presenting an aura associated with and representative of the current physiological state being sensed.

3. The bio-feedback system according to claim 2, wherein a color of the color accents may be appropriately altered in a predefined manner determined by the physiological parameter values received from the sensors and processed by the computing means.

4. The bio-feedback system according to claim 3, wherein the computing means is capable of storing images and physiological parameter values for the subject monitored for later review.

5. The bio-feedback system according to claim 3, further including a sound output unit to support a presentation of sound information to the subject, the sound information provided to attempt to further enhance the ability of the subject to possibly alter and self-regulate the subject's current physiological state.

6. The bio-feedback system according to claim 3, wherein the plurality of physiological parameter sensors include contact and non-contact sensors.

7. The bio-feedback system according to claim 6, wherein the contact sensors include at least one sensor type selected from a group comprised of pulse rate sensors, skin temperature sensors, galvanic skin impedance sensors, blood pressure sensors, and pH sensors; the plurality of contact sensors enabling the collection of physiological parameter values of the subject the sensors are contacting.

8. The bio-feedback system according to claim 6, wherein the plurality of non-contact sensors include at least one sensor type selected from a group comprised of infrared emission sensors, R-F emission sensors, and E-M field emission sensors; the plurality of non-contact sensors enabling a collection of physiological parameter values associated with radiated emissions from the subject.

9. A bio-feedback system to support monitoring and collecting of a plurality of physiological parameter values of a subject, the bio-feedback system subsequently processing the physiological parameter values to determine and present to the subject a succession of continually updated presentation states that correspond to a current physiological state of the subject, the bio-feedback system comprising:

(a) a plurality of contact and non-contact physiological parameter sensors, each sensor arranged to sense at least one physiological parameter value of the subject;

(b) computing means, operatively coupled to the sensors to enable the computing means to receive the parameter values sensed by the sensors and process the parameter values to determine and provide the presentation states to the subject;

(c) a digitizing camera arranged to continually capture an image of the subject, each captured image received and possibly stored by the computing means; and (d) a display unit, operatively coupled to the computing means to receive from the computing means images of the subject captured by the digitizing camera to enable the images to be presented to the subject; the display unit further receiving from the computing means at least one of text and graphics information, along with at least one color accent provided as at least one curved band of color coextensive with and juxtaposed to an outline of the image of the subject captured by the digitizing camera that is representative of the current physiological state being sensed.

10. The bio-feedback system according to claim 9, further including a storage unit to store at least a portion of the physiological parameter values collected, and to possibly store a plurality of the presentation states provided to the subject.

11. The bio-feedback system according to claim 9, wherein a color of the color accents may be appropriately altered by the computing means in a predefined manner determined by changes in at least one of the physiological parameter values received from the sensors and processed by the computing means.

12. The bio-feedback system according to claim 11, further including a mechanical device, wherein the parameter values collected and processed are utilized to control the mechanical device to attempt to enhance the subject's ability to monitor and possibly alter the subject's current physiological state.

13. The bio-feedback system according to claim 12, wherein the mechanical device includes at least one vibration generating device suitably coupled to the subject to enable the bio-feedback system to vary a level of vibration as the physiological state of the subject varies.

* * * * *